US006422057B1

(12) United States Patent
Anderson

(10) Patent No.: US 6,422,057 B1
(45) Date of Patent: Jul. 23, 2002

(54) DRUG PUMP TESTING SYSTEM AND METHODS

(75) Inventor: Keith B. Anderson, Wyoming, MN (US)

(73) Assignee: Deltec, Inc., St. Paul, MN (US)

( * ) Notice: Subject to any disclaimer, the term of this patent is extended or adjusted under 35 U.S.C. 154(b) by 0 days.

(21) Appl. No.: 09/162,672

(22) Filed: Sep. 29, 1998

(51) Int. Cl.[7] .............................................. F04B 51/00
(52) U.S. Cl. ......................... 73/1.36; 73/168; 604/153; 604/250
(58) Field of Search ..................... 73/1.36, 168, 1.74; 128/DIG. 12, DIG. 13; 417/475, 477.2; 604/34, 67, 131, 132, 151, 153, 246, 250

(56) References Cited

U.S. PATENT DOCUMENTS

| 4,559,038 A | | 12/1985 | Berg et al. ................... 604/153 |
| 4,650,469 A | | 3/1987 | Berg et al. ................... 604/131 |
| 4,871,439 A | * | 10/1989 | Enzer et al. ................. 204/401 |
| 5,197,322 A | * | 3/1993 | Indravudh ................ 73/1.36 X |
| 5,378,231 A | * | 1/1995 | Johnson et al. ............... 604/67 |
| 5,431,174 A | * | 7/1995 | Knute ......................... 128/898 |
| 5,531,697 A | | 7/1996 | Olsen et al. ................. 604/131 |
| 5,669,877 A | | 9/1997 | Blomquist .................... 604/67 |
| 5,695,473 A | | 12/1997 | Olsen ......................... 604/153 |
| 5,882,602 A | * | 3/1999 | Savage et al. .............. 422/103 |
| 5,902,253 A | * | 5/1999 | Pfeiffer et al. .............. 600/584 |

* cited by examiner

Primary Examiner—Thomas P. Noland
(74) Attorney, Agent, or Firm—Merchant & Gould P.C.

(57) ABSTRACT

A drug pump testing system and method comprise a pump control module having tube engaging members, with the pump control module coupled to a calibration cassette. The calibration cassette houses a reservoir bag comprising a fluid chamber and a collection area. The fluid chamber contains a known test volume prior to the initiation of the test cycle. The fluid chamber of the reservoir bag is coupled with a tube leading to the collection area, and the tube is positioned along the calibration cassette for occlusion by the tube engaging members of the pump control module. The reservoir bag comprises a fluid chamber and a collection area. The cassette can be a dual purpose cassette which tests sensors on the pump control module and also tests the accuracy of the pump control module.

11 Claims, 5 Drawing Sheets

DRUG PUMP TESTING SYSTEM AND METHODS

FIELD OF THE INVENTION

The present invention relates generally to drug pump testing systems and methods for drug pumps. In particular applications, drug pump testing systems and methods are provided for calibrating the pump mechanism of the pump. Testing systems and methods are also provided for testing one or more sensors on the pump.

BACKGROUND OF THE INVENTION

In medical applications, fluid must sometimes be conveyed intravenously to a patient undergoing treatment. The fluid is usually contained in a fluid reservoir, typically a bag, conveyed through a tube, and injected into the patient's vein. Many times, regulating the volume and rate the fluid is conveyed to the patient is advantageous, and in such instances, traditionally, infusion pumps are employed.

One such infusion pump effective for the application described above is disclosed is U.S. Pat. No. 4,559,038 ("the '038 patent"), the disclosure of which is herein incorporated by reference. The infusion pump disclosed therein regulates the conveyance of fluid from a fluid reservoir to a patient. In accordance with the infusion pump of the '038 patent, a reservoir containing fluid for treating a patient is held in a cassette having a pressure plate immediately adjacent to a pump control module. A tube for conveying the fluid couples the fluid reservoir and the patient and provides a medium for conveying the fluid. A pump control module regulates the rate fluid is conveyed to the patient by applying physical pressure to the tube, thereby restricting the volume of fluid flow. In the '038 patent, the pump control module includes a pumping mechanism having tube engaging members which engage and squeeze the tube against the pressure plate of the cassette. The tube engaging members of the '038 patent include an expulsor and an inlet valve and an outlet valve on opposite sides of the expulsor.

Infusion pump systems and methods, particularly when used in medical applications, must perform with accuracy. Using an infusion pump to deliver medication and/or other fluid to a patient requires an accurate pumping mechanism. To ensure that an infusion pump performs with the requisite accuracy, testing is conducted on infusion pumps used for these applications. Typically, the testing equipment used and methods performed to measure the accuracy of the infusion pump and associated pumping mechanism are expensive and cumbersome. In such typical setups, a calibrated scale, a fluid reservoir, a recipient container, and a timing device are necessary equipment. Further, performing this testing procedure requires a significant amount of time for assembly and disassembly, consumes space, and requires a skilled operator to correctly perform the test. U.S. Pat. No. 5,669,877 ("the '877 patent"), commonly owned with the '038 patent, relates to automated testing of drug pumps with a testing device and a computer. The disclosure of the '877 patent is hereby incorporated by reference.

The pump control module may include various sensors used during pump operation. It is desirable to verify the proper functioning of the sensors. Examples of sensors used with infusion pumps include cassette identification sensors and tube occlusion sensors. U.S. Pat. No. 5,531,697 (the '697 patent) concerns a pump including a cassette identification system having one or more sensors for sensing indicia on the cassette relating to the type of drug or fluid to be pumped, concentration, volume, the amount of drug pumped per activation of the pump, i.e., tube size. Also, the cassette identification system can be used to prevent operation of the pump if an unauthorized cassette is coupled to the pump control module. U.S. Pat. No. 5,695,473 (the '473 patent) concerns a pump having an occlusion sensing system with at least one sensor. U.S. Pat. No. 4,650,469 (the '469 patent) also concerns a pump having an occlusion sensing system. These patents are also commonly owned with the '038 patent, and the disclosures are hereby incorporated by reference.

There is a continued need for further testing systems and methods, especially for pump mechanism calibration and sensor testing.

SUMMARY OF THE INVENTION

In one aspect the present invention comprises a calibration cassette for a drug pump testing system. The calibration cassette comprises a housing supporting a reservoir bag wherein the reservoir bag contains a known test volume. The housing of the calibration cassette has at least one opening for a tube communicating between the reservoir bag and a collection area to pass, and the tube is preferably positioned along a top surface of the calibration cassette. The collection area is housed substantially within the housing of the calibration cassette. A variation of this calibration cassette comprises a reservoir bag having a dual chamber: a fluid chamber and a collection chamber separated by a barrier.

Another aspect of the drug pump testing system of the present invention comprises a pump control module having tube engaging members and coupled to a calibration cassette. The calibration cassette of the drug pump testing system houses a reservoir bag comprising a fluid chamber and a collection area, and the fluid chamber contains a known test volume. The reservoir bag is coupled with a tube communicating between the fluid chamber and the collection area. The tube is positioned along the calibration cassette and positioned for occlusion by the tube engaging members.

In yet another aspect, the present invention comprises a method for calibrating a pump. This method comprises steps including providing a pump control module coupled to a calibration cassette. The calibration cassette supports a fluid chamber which contains a known test volume. A tube communicating between the fluid chamber and a collection area and an occlusion sensor is also provided. The tube is positioned for occlusion by tube engaging members of the pump control module, and the known test volume is pumped from the calibration cassette to the collection area. Each stroke of the tube engaging members is counted to obtain a number of pump strokes. After the known test volume has been completely pumped from the fluid chamber, the pump control module is stopped. A display of the pump control module displays indicia indicative of the accuracy of the pump control module.

Another aspect of the invention concerns a method for testing a drug pump comprising the steps of providing a pump control module, comprising at least one occlusion sensor, coupled to a bottom surface of a calibration cassette having a sensor testing mode cassette identification projection and at least one pressure protrusion delivering a known pressure. The output of the at least one occlusion sensor is compared with the known pressure. Then, the bottom surface of the calibration cassette is uncoupled from the pump control module, and the top surface of the calibration cassette is coupled to the pump control module. A tube is provided so that the tube communicates between a known test volume and a collection area and is positioned for occlusion by tube engaging members of the pump control module. The volume of the known test volume is input into the pump control module, and the known test volume is pumped from the calibration cassette to the collection area. Once the pumping is complete as sensed by the one or more occlusion sensors, the pumping step is stopped. The accuracy of the pump control module is determined by reading the difference between the product of the number of pump strokes and the nominal pump stroke volume and the known test volume as output by the pump.

DETAILED DESCRIPTION

Figure 1:
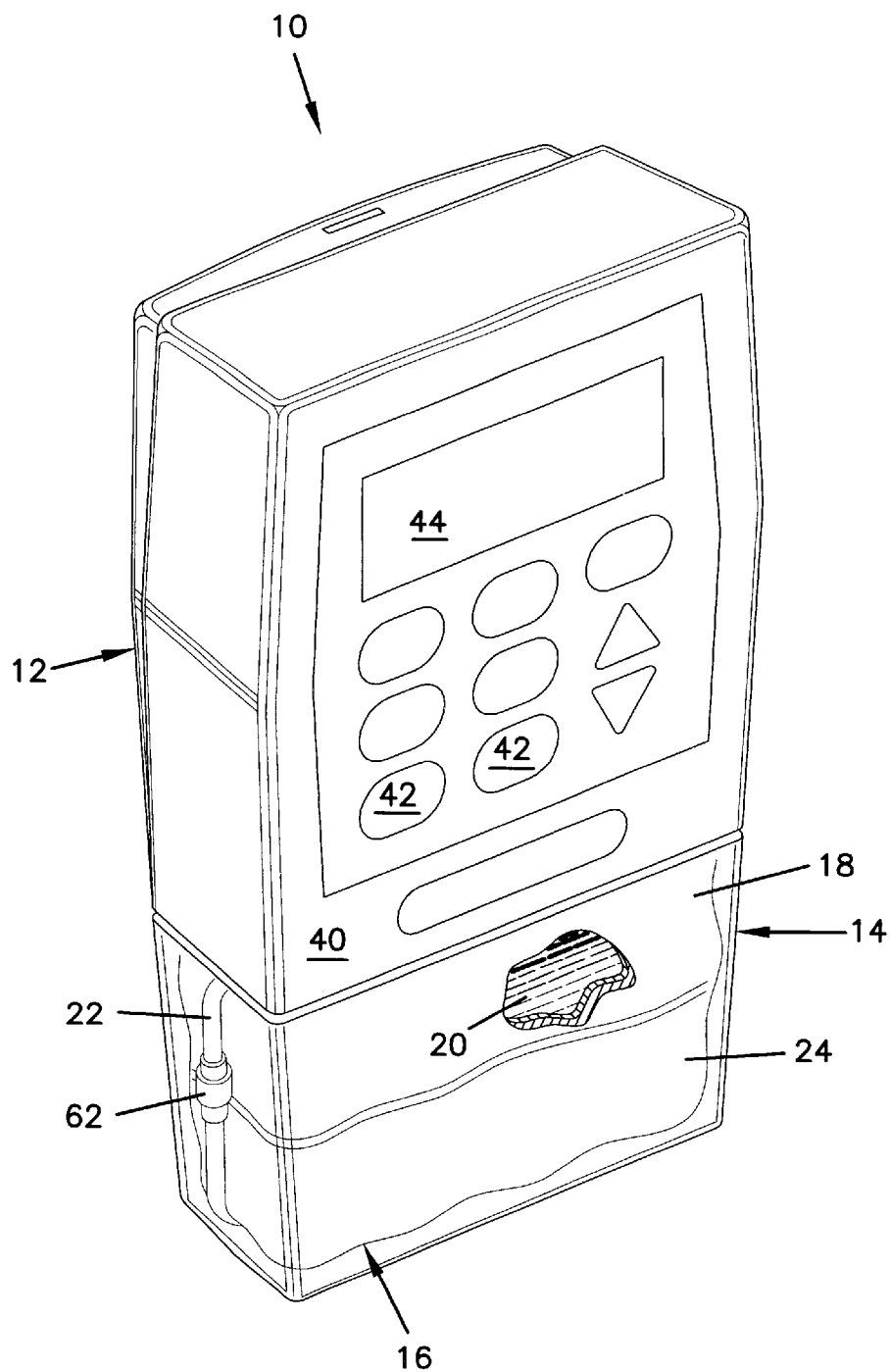
FIG. 1 is a perspective view of a drug pump testing system in accordance with the present invention comprising a pump control module coupled to a calibration cassette.

This invention relates to a drug pump testing system and method for calibrating a pump. The present invention is preferably used to calibrate infusion pumps, and particularly infusion pumps regularly employed for medical applications. In general, the drug pump testing system and method of the present invention includes a pump control module and a calibration cassette which houses a reservoir bag comprising a fluid chamber for holding a known test volume prior to the initiation of a test cycle.

The calibration cassette is coupled to the pump control module so that tube engaging members of the pump control module are positioned to act on a tube communicating between the fluid chamber and the collection area. The tube is preferably positioned along a top surface of the calibration cassette where an engagement portion of the tube is successively contacted by tube engaging members of the pump control module to effect pumping. The tube engaging members of the pump control module, which can comprise an expulsor and an inlet valve and an outlet valve, disposed on opposite sides of the expulsor, are positioned to successively contact the engagement section of the tube to effect pumping.

The calibration cassette preferably contains a known test volume which is pumped from within the housing of the calibration cassette to a collection area. Comparing the volume pumped according to the nominal stroke value of the pump control module with the known test volume permits the user or the pump control module itself to ascertain the accuracy of the pump control module. The drug pump can then be calibrated or otherwise adjusted appropriately.

In accordance with some embodiments of the present invention, various sensors are incorporated into the pump control module. While numerous types and forms of sensors exist, sensors capable of detecting the type of cassette coupled to the pump control module and occlusion sensors for detecting and/or locating occlusions in the tube and ascertaining pressure variations have been found to be highly beneficial when used with the drug pump testing system and methods of the present invention. These sensors are generally incorporated into the pump control module and are designed to work in conjunction with features on cassettes used with the pump control modules of the type discussed herein. For purposes of the present invention, the calibration cassette of some embodiments of the invention comprises additional features for accommodating sensors on the pump control module.

Another aspect of the present invention involves the testing of the various sensors incorporated into the pump control module. Some embodiments of the drug pump testing system and methods of the present invention concern efficient and accurate equipment and methods for testing the sensor or sensors incorporated into the pump control modules. Specifically, the invention provides equipment for testing the cassette identification sensor and for testing occlusion sensors on embodiments of the pump control modules comprising such features.

One aspect of the invention is to initiate the drug pump testing methods of the present invention by first testing the sensors incorporated into the pump control module before conducting the calibration testing discussed herein. These sensors, more specifically the cassette identification sensor and the one or more occlusion sensors, are used in performing the calibration test, thus ensuring that the sensors are accurately and properly operating further ensures a successful calibration test.

Once the sensors are tested and determined to be working properly, the test cycle for calibration testing is commenced and pumping is initiated. The known test volume is pumped, and the test cycle is complete when the known test volume has been entirely pumped from the fluid chamber to a collection area. In some embodiments, the occlusion sensor incorporated in the drug pump testing system is triggered when the fluid chamber is empty, at which time pumping ceases. In some embodiments of the present invention, the occlusion sensor, once triggered, stops the tube engaging members from pumping, either automatically or manually, so that the number of strokes of the pumping mechanism can be counted. The occlusion sensor either triggers an alarm to inform the test system operator that the known test volume has been pumped or triggers a stopping mechanism in the pump control module to stop the tube engaging members from effecting pumping automatically.

After the test cycle has completed, the volume of fluid which should have been pumped, according to the pump stroke volume of the pump control module multiplied by the number of strokes made by the pump during the test cycle, is compared to the known test volume. If the volume which should have been pumped, given the pump stroke volume and the number of strokes during the test cycle, differs from the known test volume, the pump control module must be calibrated and/or otherwise adjusted for accuracy. Some of the more advanced pump control modules used with the device and method of the present invention are capable of automatically self-calibrating. Conducting multiple tests permits the precision of the infusion pump to be determined.

These features of novelty and various other advantages which characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described a preferred embodiment of the invention. Reference will now be made in detail to preferred embodiments of the present invention wherein like reference numerals indicate like elements through the several views shown in FIGS. 1 through 6.

As embodied herein and illustrated in FIG. 1, the drug pump testing system is shown generally at 10 and comprises a pump control module 12 coupled with a calibration cassette 14. The calibration cassette 14 preferably houses a reservoir bag 16 comprising a fluid chamber 18 containing a known test volume 20. The known test volume 20 is pumped through a tube 22 during the test cycle, and the tube 22 preferably communicates between the fluid chamber 18 and a collection area 24 in the calibration cassette 14.

Figure 2:
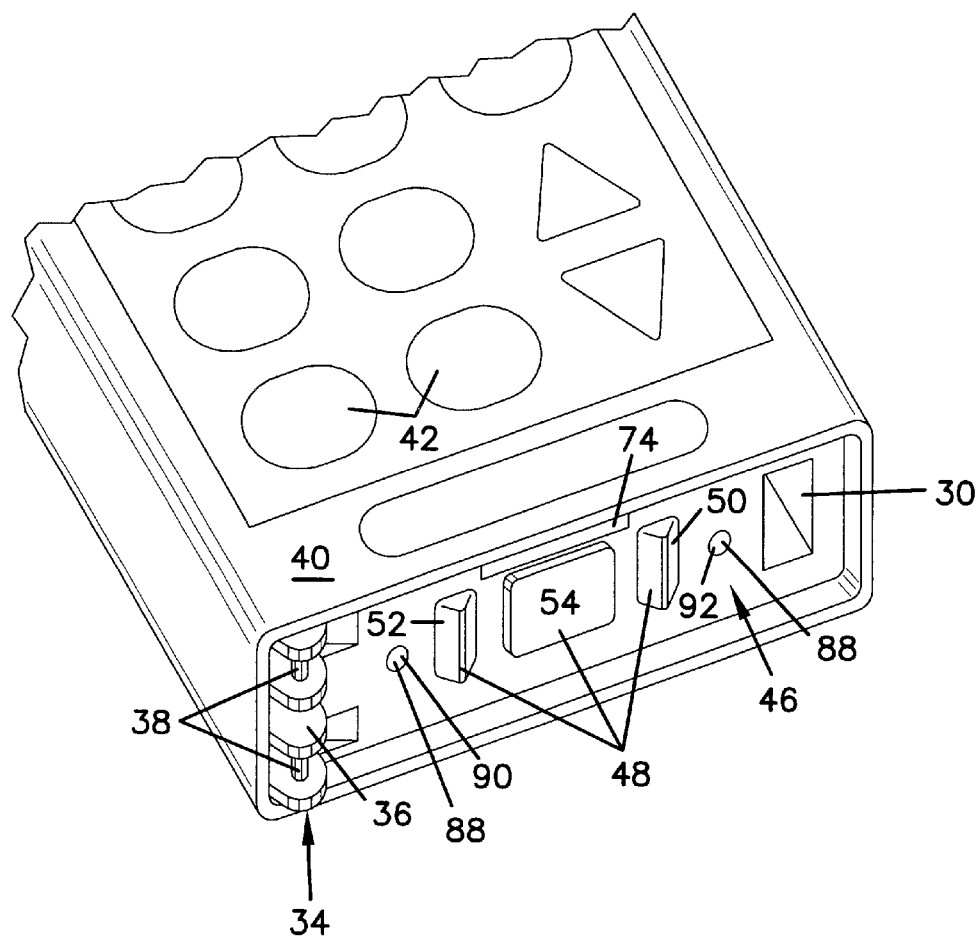
FIG. 2 is a perspective view of a tube interface region of the pump control module of FIG. 1.
Figure 3:
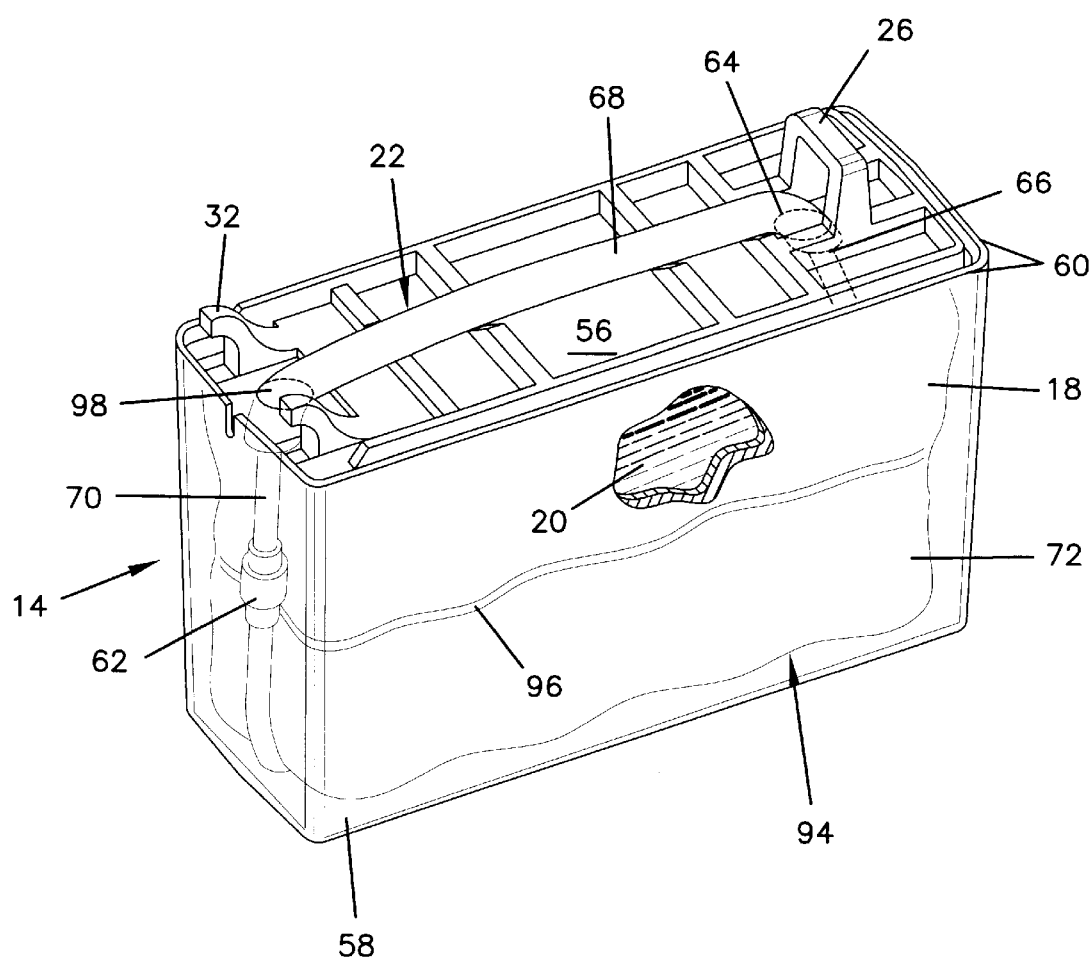
FIG. 3 is a perspective view of the calibration cassette of FIG. 1 showing a pressure plate of the calibration cassette.

In the preferred embodiments of the drug pump testing system 10 of the present invention, the calibration cassette 14 is secured to the pump control module 12 through the use of an anchor 26, as shown in FIG. 3, incorporated into the calibration cassette 14. The anchor 26 is preferably engaged by a releasable securing mechanism (not shown) inside a cavity 30 of the pump control module 12 (shown in FIG. 2). The calibration cassette 14 is additionally secured to the pump control module 12 with at least one pump securing extension 32, also shown in FIG. 3. The pump securing extensions 32 preferably engage a suspended pin assembly 34 or similar structure as shown in FIG. 2. The pin assembly 34 preferably comprises support structure 36 on the pump control module 12 (see FIG. 2) for retaining a pin 38.

Referring again to FIG. 1, the pump control module 12 of the present invention preferably includes a control and display face 40. The control and display face 40 of the embodiment shown comprises a plurality of control keys 42 for operating the pump control module 12 and a display 44 for conveying input and output information to the test system operator. While most embodiments of the present invention incorporate displays 44 which convey information in digital form, those of ordinary skill in the art will recognize that some alternative displays function equally well.

A tube interface region 46, as best shown in FIG. 2, is preferably positioned substantially orthogonal to the control and display face 40 on the pump control module 12 of the present invention. The tube interface region 46 preferably comprises tube engaging members 48 which apply mechanical pressure to the tube 22, thereby, capable of pumping the known test volume 20 during the test cycle. The tube engaging members 48 shown in FIG. 2 comprise an inlet valve 50 and an outlet valve 52 disposed on opposite sides of an expulsor 54. When the calibration cassette 14 is properly secured to the pump control module 12 while the tube 22 is properly positioned, the tube engaging members 48 of the pump control module 12 selectively contact the tube 22 to effect pumping while at the same time preventing free flow. The '038 patent referenced herein above, includes a similar tube interface region 46 with three tube engaging members 48. The expulsor 54 and the valves 50, 52 move from a retracted position to an extended position to deform the tube 22, thereby effecting pumping through the tube 22. The selective contact of the tube engaging members 48 on the tube 22 also prevents backflow, i.e., prevents any fluid from flowing in the wrong direction through the tube 22.

As shown in FIG. 3, the calibration cassette 14 includes a top surface 56 and a housing 58. In preferred embodiments of the present invention, edges 60 of the top surface 56 are secured to the housing 58 to prevent tampering or interference with the contents of the calibration cassette 14. The housing 58 of the calibration cassette 14 preferably contains the reservoir bag 16 comprising the fluid chamber 18 for containing the known test volume 20 prior to the initiation of the test cycle.

The fluid chamber 18 of the reservoir bag 16 is preferably pre-filled with a precisely known fluid volume, or the known test volume 20. The known test volume 20 preferably has an exact volume corresponding to an integer multiple of the nominal stroke volume of the pump control module 12. Selecting the known test volume 20 in this manner simplifies calculations necessary for proper calibration.

As explained briefly herein above, comparing the known test volume 20 to the volume the pump control module 12 calculates has been pumped determines the accuracy of the drug pump and whether the drug pump is properly calibrated or requires adjustment. The volume of fluid which should have been pumped, according to the pump stroke volume of the pump control module 12 multiplied by the number of strokes made by the pump during the test cycle, is compared to the known test volume 20. If the volume which should have been pumped, given the pump stroke volume of the pump control module 12 and the number of strokes during the test cycle, differs from the known test volume 20, the pump control module 12 is in need of calibration and/or adjustment. Some of the more advanced pump control modules 12 used with the device and method of the present invention are capable of automatically self-calibrating. Conducting multiple tests permits the precision of the infusion pump to be determined.

All air and/or other fluid is removed from the fluid chamber 18 to ensure that only the known test volume 20 is pumped through the tube 22 during the test cycle. The fluid chamber 18 of the reservoir bag 16 is preferably pre-filled with the known test volume 20 by the manufacturer of the calibration cassette 14. The housing 58 of the calibration cassette 14 of some preferred embodiments of the present invention is not accessible after manufacture to ensure that the known test volume 20 is not tampered with, although alternative embodiments of the drug pump testing system 10 of the present invention comprise housings 58 which are openable for accessing the reservoir bag 16. Having the volume of fluid of the known test volume 20 printed on the calibration cassette 14 has been found to be beneficial. The known test volume 20 contained in the fluid chamber 18 must be known to successfully and accurately use the drug pump testing system 10 and perform the methods of the present invention. Thus, precautions are preferably taken to ensure that the known test volume 20 does not change between manufacture and use. A preferred embodiment of the calibration cassette 14 of the drug pump testing system 10 of the present invention comprises the housing 58 secured to the top surface 56 and supporting the fluid chamber 18 containing the known test volume 20.

Some embodiments of the present invention further comprise an anti-siphon valve 62 incorporated into the tube 22 to prevent fluid flow from the fluid chamber 18 prior to use. Alternative precautionary measures are known and available in the relevant art. Incorporating the anti-siphon valve 62 has been found to be particularly advantageous in applications of the present invention when a substantial period of time elapses between the manufacture of the calibration cassette 14 and its use.

The tube 22 communicates with the fluid chamber 18 of the reservoir bag 16 for conveying the known test volume 20 from the fluid chamber 18 to the collection area 24 during the test cycle. The tube 22 preferably leads from the fluid chamber 18 of the reservoir bag 16 within the calibration cassette 14 through an opening 64 in the calibration cassette 14, across the top surface 56 of the calibration cassette 14, and finally to the collection area 24. The tube 22 used with the present invention generally comprises three sections: an upstream section 66, an engagement section 68, and a downstream section 70.

The upstream section 66 is the portion of the tube 22 which carries the known test volume 20 from the fluid chamber 18 of the reservoir bag 16 to the engagement section 68 of the tube 22 during the test cycle. The upstream section 66 of the tube 22 extends from the fluid chamber 18 within the calibration cassette 14 through the opening 64, which is preferably positioned in either the top surface 56 or the housing 58 of the calibration cassette 14. The opening 64 is shown (in phantom lines) in the top surface 56 of the calibration cassette 14 depicted in FIG. 3.

Figure 4:
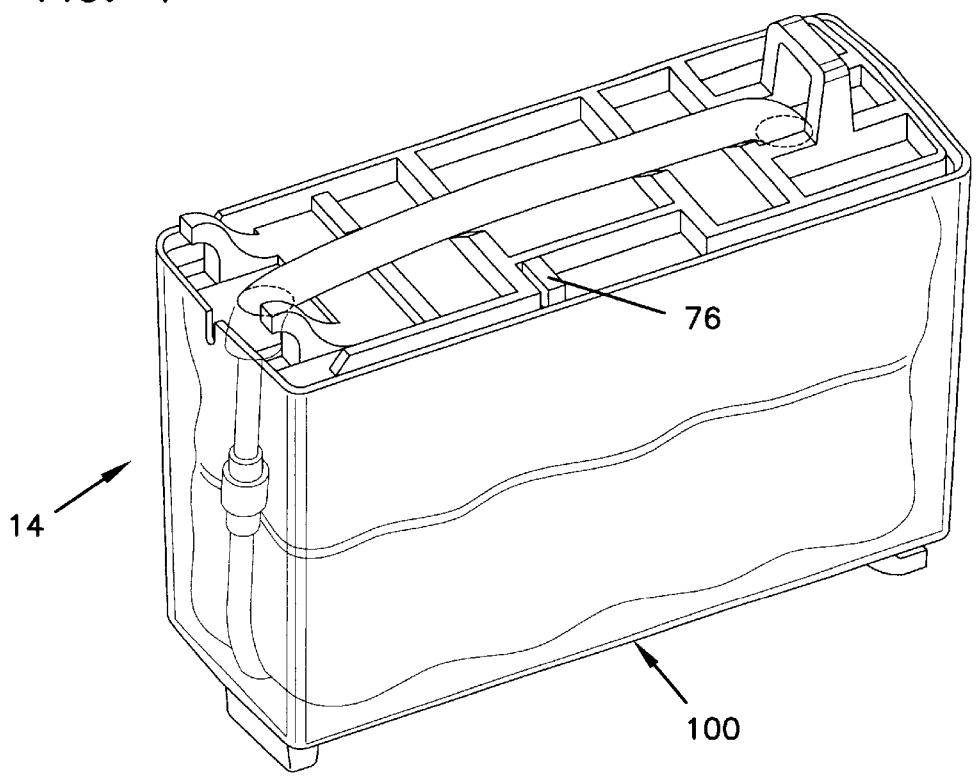
FIG. 4 is a perspective view of a calibration cassette comprising a top surface and a bottom surface, the top surface having a calibration mode cassette identification projection.

The engagement section 68 is the portion of the tube 22 which extends along the top surface 56 of the calibration cassette 14. The engagement section 68 of the tube 22 is successively contacted by the tube engaging members 48 of the pump control module 12 to effect pumping during the test cycle. The engagement section 68 of the tube 22 of some preferred embodiments of the drug pump testing system 10 is of relatively larger diameter than the upstream section 66 and the downstream section 70 of the tube 22. This relative difference in diameter between the upstream section 66 and downstream section 70 of the tube 22 and the engagement section 68 of the tube 22 is best shown in FIGS. 3 and 4.

The engagement section 68 the tube 22 is preferably substantially longitudinally aligned with the top surface 56 of the calibration cassette 14 when the tube 22 is properly installed and positioned in the calibration cassette 14 of the present invention. As shown in FIG. 3, the engagement section 68 of the tube 22 lies substantially along a longitudinal centerline of the top surface 56 of the calibration cassette 14. While the engagement section 68 of the tube 22 is proximate relative to the tube engaging members 48 when the calibration cassette 14 is coupled to the pump control module 12, the downstream section 70 of the tube 22 leads to the collection area 24.

The downstream section 70 of the tube 22 carries the fluid of the known test volume 20 away from the fluid chamber 18 during pumping and preferably to the collection area 24. The collection area 24 either collects the pumped known test volume 20 or disposes of the known test volume 20 after the known test volume 20 has been pumped from the fluid chamber 18 and through the tube 22. The downstream section 70 of one embodiment of the drug pump testing system 10 of the present invention simply leads to a drain (not shown) which carries the known test volume 20 away after the test cycle has completed. The downstream section 70 of another embodiment of the drug pump testing system 10 of the present invention leads to a collection chamber 72 within the housing 58 of the calibration cassette 14 where the known test volume 20 is collected after pumping.

Various sensors can be incorporated into the pump control module 12 of the type typically used in conjunction with the present inventions. Two types of sensors have been found to be particularly useful in conducting the tests and methods described herein. A sensor for detecting and identifying the type of cassette coupled to the pump control module 12, or a cassette identification sensor 74, is often advantageous for conveying information to the drug pump operator about the type of cassette in use and/or for automatically adjusting the pump control module 12 to function with the calibration cassette 14. For example, the cassette identification sensor 74 incorporated into the pump control module 12 for use with the present invention preferably recognizes some identifying indicia or feature arranged on the calibration cassette 14 and automatically shifts the pump control module 12 into a calibration testing mode. As an alternative, the cassette identification sensor 74 of the pump control module 12 could recognize some identifying indicia or feature arranged on the calibration cassette 14 and convey, through the control and display face 40, information to the pump operator concerning the type of the calibration cassette 14, or other cassette, which has been coupled to the pump control module 12. The pump operator could then manually adjust the pump control module 12 to accommodate the calibration cassette 14.

Figure 6:
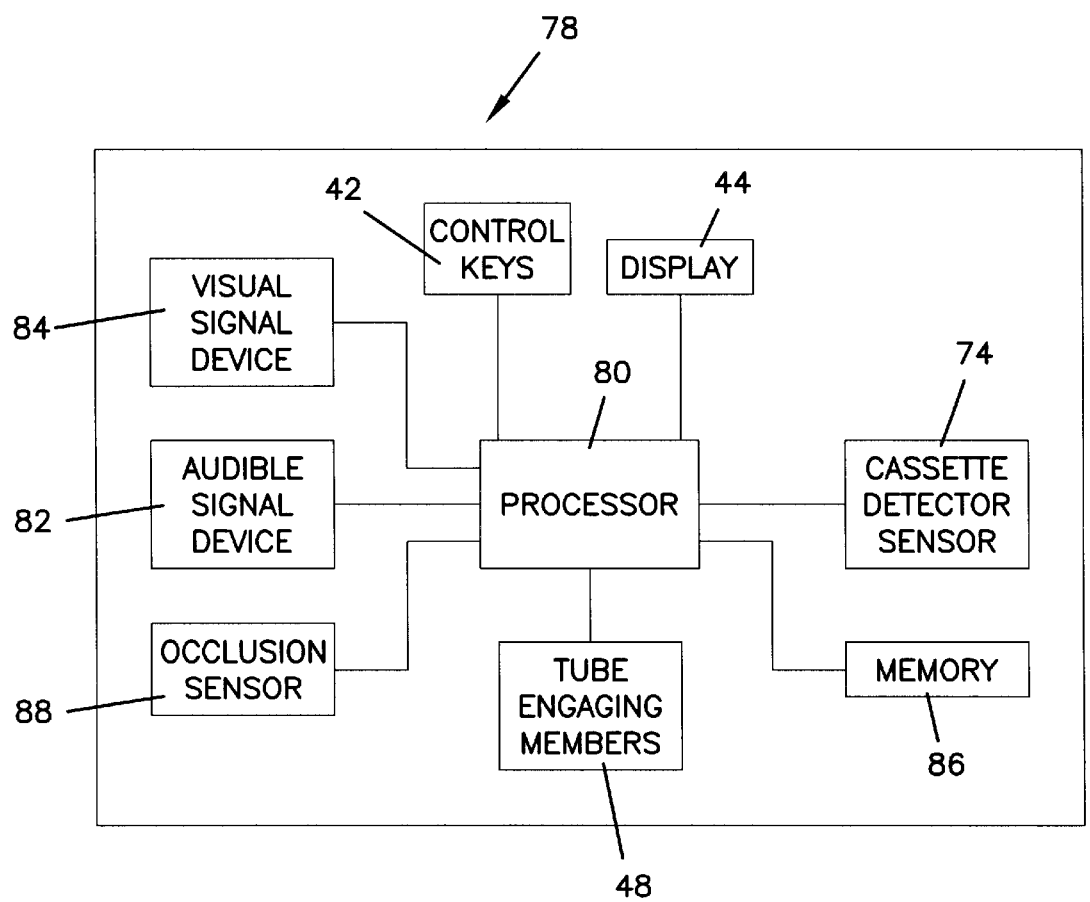

The pump control module 12 of preferred embodiments of the present invention can automatically enter into the calibration mode through its sensing of a cassette identifying feature 76. Equipment and methods such as this are described in the '697 patent, the disclosure of which was previously incorporated by reference herein. In the embodiment of the present invention shown in FIG. 4, the cassette identifying feature 76 of the calibration cassette 14 comprises a projection extending from the top surface 56 of the calibration cassette 14, and the cassette identifying feature 76 interacts with the cassette identification sensor 74 of the pump control module 12 as shown in FIG. 2. Other types of cassette identification systems exist and include, for example, a light reflecting system which utilizes light from the pump control module 12 which is reflected off the cassette (not shown). Still other types of cassette identification systems incorporate other contact and non-contact switches or sensors to sense indicia on the cassette to identify the cassette from a plurality of other cassettes. FIG. 6 is a schematic diagram of a control system 78 of the pump control module 12 incorporating the above-described system.

Referring now to FIG. 6, the control system 78 for the pump control module 12 which comprises the cassette identification sensor 74 similar to that described above, is shown. The control system 78 includes a processor 80 electronically interconnected to the control keys 42, the display 44, the tube engaging members 48, and the cassette identification sensor 74 of the pump control module. The embodiment of FIG. 6 also comprises an audible signal device 82 and a visual signal device 84 interconnected to the processor 80. The control system 78 further includes a memory 86 for storing various programs for operating the pump control module 12. For example, the control system 78 used with the present invention preferably contains a program which recognizes when the calibration cassette 14 of the present invention is coupled to the pump control module 12 and, thus, sets the pump control module 12 to a calibration testing mode. Various additional features can be incorporated into this system and the details of those features are more fully explained in the disclosure of the '697 patent.

Another type of sensor which has been found a favorable feature for use with the drug pump testing system 10 of the present invention is at least one occlusion sensor 88. One such occlusion sensor 88 is shown in FIG. 2 associated herewith. The one or more occlusion sensors 88 contained in the pump control module 12 preferably sense pressure variations in the tube 22 and, at some minimal pressure, indicate that the fluid chamber 18 is empty and stop the tube engaging members 48 of the pump control module 12 from acting on the tube 22. In addition to sensing pressure variations, the occlusion sensors 88 used in conjunction with the present invention are also preferably sensitive to complete occlusions or blockages and immediately notify the pump operator and/or stop pumping. The occlusion sensors 88 monitor pressure conditions in the fluid pressure upstream and downstream of the tube engaging members 48 and detect upstream and/or downstream occlusions. In the calibration mode of the present invention, the number of pump strokes can then be counted either automatically or manually once the occlusion sensors 88 detect that the fluid chamber 18 is empty.

In one embodiment of the present invention, the occlusion sensor 88 preferably comprises a signal, such as an alarm, which signals the test system operator to stop the pump control module 12 and ascertain the number of pump strokes completed during the test cycle. The alarm can be visual, audible, tactible or any combination thereof. These alarms are discussed in greater detail in the '473 patent, the disclosure of which has been herein incorporated by reference. An alternative and more sophisticated embodiment of the occlusion sensor 88 which can be used with the present invention comprises a system which automatically stops the pump control module 12 once the known test volume 20 has been pumped from the fluid chamber 18 to the collection area 24—i.e., the test cycle is completed. In some embodiments of the present invention, the occlusion sensor 88 makes possible one or more of the following functions: counts the pump strokes at the completion of the test cycle; calculates the volume the pump control module 12 should have pumped given the number of strokes and nominal pump stroke volume; and/or compares the known test volume 20 with the product of the nominal pump stroke volume and the number of strokes. The drug pump testing system 10 of the present invention may include an outlet sensor 90 for determining the pressure in the tube 22 downstream from the outlet valve 52, and an inlet sensor 92 for determining fluid pressure upstream of the inlet valve 50. These sensors 90, 92 are discussed in greater detail in the '473 patent.

In alternative embodiments of the present invention, the downstream section 70 of the tube 22 leads to the collection chamber 72 incorporated into the reservoir bag 16 where the known test volume 20 is retained after the test cycle has completed. One embodiment of the present invention comprises a dual chamber reservoir bag 94 used in connection with the drug pump testing system 10. This embodiment can be preferable because the testing system 10 of this embodiment is wholly self-contained and requires no accommodation to implement the device or method once the calibration cassette 14 is coupled to the pump control module 12.

One preferred embodiment of the present invention comprising the dual chamber reservoir bag 94 is shown in FIG. 3. In this embodiment of the drug pump testing system 10, the housing 58 of the calibration cassette 14 contains the dual chamber reservoir bag 94. The dual chamber reservoir bag 94 comprises the fluid chamber 18 and the collection chamber 72 substantially separated from one another by a barrier 96. The barrier 96 can be integrated into the dual chamber reservoir bag 94. Only when the test cycle initiates is the known test volume 20 permitted to flow to the collection chamber 72 of the dual chamber reservoir bag 94.

In embodiments of the present invention comprising the dual chamber reservoir bag 94, the downstream section 70 of the tube 22 preferably begins at the engagement section 68 of the tube 22 and leads into a second opening 98 in either the top surface 56 or the housing 58 of the calibration cassette 14. The downstream section 70 of the tube 22 preferably communicates with the collection chamber 72 and carries the known test volume 20 to the collection chamber 72 during the test cycle. In most embodiments of the present invention, the second opening 98 will be at the end of the calibration cassette 14 opposite to the opening 64 though which the upstream section 66 of the tube 22 extends from the fluid chamber 18.

Like other embodiments of the present invention, the drug pump testing system 10 incorporating the dual chamber reservoir bag 94 preferably incorporates the anti-siphon valve 62 to prevent the known test volume 20 from flowing out of the fluid chamber 18 and into the collection chamber 72 prior to use.

One embodiment of the calibration cassette 14 of the present invention comprises the top surface 56 comprising the anchor 26 and the pump securing extensions 32 discussed above and further comprises a bottom surface 100 also comprising the anchor 26 and the pump securing extensions 32 which can, alternatively, be used to couple the calibration cassette 14 to the pump control module 12. The bottom surface 100 of the calibration cassette 14 comprises special features, including at least one pressure protrusion 102 generally incorporated by molding. The pressure protrusion 102 preferably exerts a predetermined pressure against one or more of the occlusion sensors 88 of the pump control module 12. Some embodiments of the system and methods of the present invention use the calibration cassette 14 equipped with two pressure protrusions 102 for use with the pump control module 12 equipped with at least two occlusion sensors 88: the inlet occlusion sensor 92 and the outlet occlusion sensor 90.

Comparing the predetermined pressure exerted by the pressure protrusions 102 on the occlusion sensors 88 of the pump control module 12 with the resulting readings and output of the pump control module 12 allows testing the occlusion sensors 88 to ensure that the occlusion sensors 88 are working properly in that they are both responsive and accurate.

Another feature which can be incorporated into the bottom surface 100 of the calibration cassette 14, is a sensor testing mode cassette identification projection 104 which can activate the cassette identification sensor or switch 74, as described above, incorporated into the pump control module 12. Thus, the pump control module 12 automatically enters into a sensor testing mode when the bottom surface 100 of the calibration cassette 14 is coupled to the pump control module 12. With the bottom surface 100 of the calibration cassette 14 correctly attached to the pump control module 12, the pump control module 12 performs a self-test of the occlusion sensors 88 and verifies that the occlusion sensor 88 readings and consequent outputs are within preset voltage limits in the pump control modules 12 comprising analog occlusion sensors 88. In pump control modules 12 comprising digital switches, attaching the bottom surface 100 of the calibration cassette 14 to the pump control module 12 can be done to verify the correct logic state.

Once this test of the occlusion sensors 88 and the readings and outputs of the occlusion sensors 88 is complete, the calibration cassette 14 is removed from the pump control module 12 and rotated so that the top surface 56 of the calibration cassette 14 can be coupled to the pump control module 12 to conduct the calibration test for the accuracy of the pump control module 12. At the initiation of the test cycle, preferably the pump control module 12 counts pump strokes, although if the pump control module 12 does not automatically count the pump strokes, the test system operator can count the pump strokes completed during the test cycle. Once the known test volume 20 has been completely pumped from the fluid chamber 18 to the collection area 24, the occlusion sensor 88 senses that the fluid chamber 18 is empty and either stops the pump control module 12 or signals the test system operator to stop the pump control module 12. After the test cycle is completed, the number of strokes of the pump control module 12 is determined, either by reading the display 44 of the pump control module 12 or by having been counted. Multiplying the volume of fluid pumped per stroke or nominal stroke volume (a constant quantity for a properly working pump control module 12) by the number of strokes equals the known test volume 20. If this calculation is performed, either automatically by the pump control module 12 or manually by the test system operator, the resulting calculated volume does not equal the known test volume 20 used in the procedure, the pump control module 12 is not calibrated properly and/or is in need of alternative adjustment or repair.

In practice, to perform an infusion pump self calibration procedure or to measure the accuracy of the pump control module 12, the test system operator couples the calibration cassette 14, preferably incorporating the reservoir bag 16 containing the known test volume 20, to the pump control module 12. Either the pump control module 12 detects the presence of the calibration cassette 14 and automatically enters a calibration mode, or the test system operator places the pump into a special calibration mode via the control keys 42 on the control and display face 40 of the pump control module 12. The test system operator can then position the downstream section 70 of the tube 22 to lead to the collection area 24, or, in some embodiments, the collection chamber 72 is housed with the fluid chamber 18 within the housing 58 of the calibration cassette 14. Once the test cycle is initiated, the pump control module 12 will pump the known test volume 20 from the fluid chamber 18, through the tube 22, and to the collection area 24.

Upon starting, the pump counts the number of pumping strokes required to empty the calibration cassette 14. The pump control module 12 preferably detects the empty calibration cassette 14 via the occlusion sensor 88. Once the known test volume 20 has been entirely pumped from the fluid chamber 18 to the collection area 24, which can be the collection chamber 24 of the dual chamber reservoir bag 94, at the conclusion of the test cycle, the occlusion sensor 88 either signals the test system operator to stop the pump control module 12, or the pump control module 12 automatically stops so that pumping ceases. Because the volume of the known test volume 20 of the pre-filled calibration cassette 14 has been entered into the pump control module 12, the nominal pumping stroke volume of the pump and the number of strokes required to empty the calibration cassette 14, the pump calculates and displays the resulting volume pumped. Alternatively, the pump control module 12 can store the calibration value to be used during subsequent deliveries. In such instances, the test can be repeated to verify delivery accuracy within desired limits with the new calibration values. Using this invention, infusion pumps can be tested for accuracy nearly anywhere by an unskilled operator at relatively low cost.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. A drug pump testing system comprising:
   (a) a pump control module having moveable tube engaging members;
   (b) a calibration cassette coupled to said pump control module;
   (c) said calibration cassette housing a reservoir bag comprising a fluid chamber and a collection area, said fluid chamber containing a known test volume;
   (d) said reservoir bag coupled with a tube communicating between said fluid chamber and said collection area; and
   (e) said tube positioned along said calibration cassette for occlusion by said tube engaging members.

2. The drug pump testing system of claim 1, wherein said pump control module has a calibration mode.

3. The drug pump testing system of claim 2, wherein said pump control module enters said calibration mode when said calibration cassette is coupled to said pump control module.

4. The drug pump testing system of claim 2, wherein said pump control module counts pump strokes of said tube engaging members.

5. The drug pump testing system of claim 1, wherein a volume of said known test volume is an integer multiple of a nominal pump stroke volume of said pump control module.

6. The drug pump testing system of claim 1, wherein said reservoir bag includes a dual reservoir bag.

7. The drug pump testing system of claim 6, wherein said dual reservoir bag further comprises a barrier separating said fluid chamber and said collection area.

8. The drug pump testing system of claim 1, wherein said pump control module further comprises at least one occlusion sensor.

9. The drug pump testing system of claim 8, wherein said occlusion sensor ceases movement of said tube engaging members of said pump control module after said known test volume is pumped to said collection area.

10. The drug pump testing system of claim 8, wherein said pump control module further comprises a sensor testing mode.

11. The drug pump testing system of claim 10, wherein said calibration cassette further comprises a bottom surface having a sensor testing mode cassette identification projection and at least one pressure protrusion.

* * * * *

UNITED STATES PATENT AND TRADEMARK OFFICE
CERTIFICATE OF CORRECTION

Figure 5:
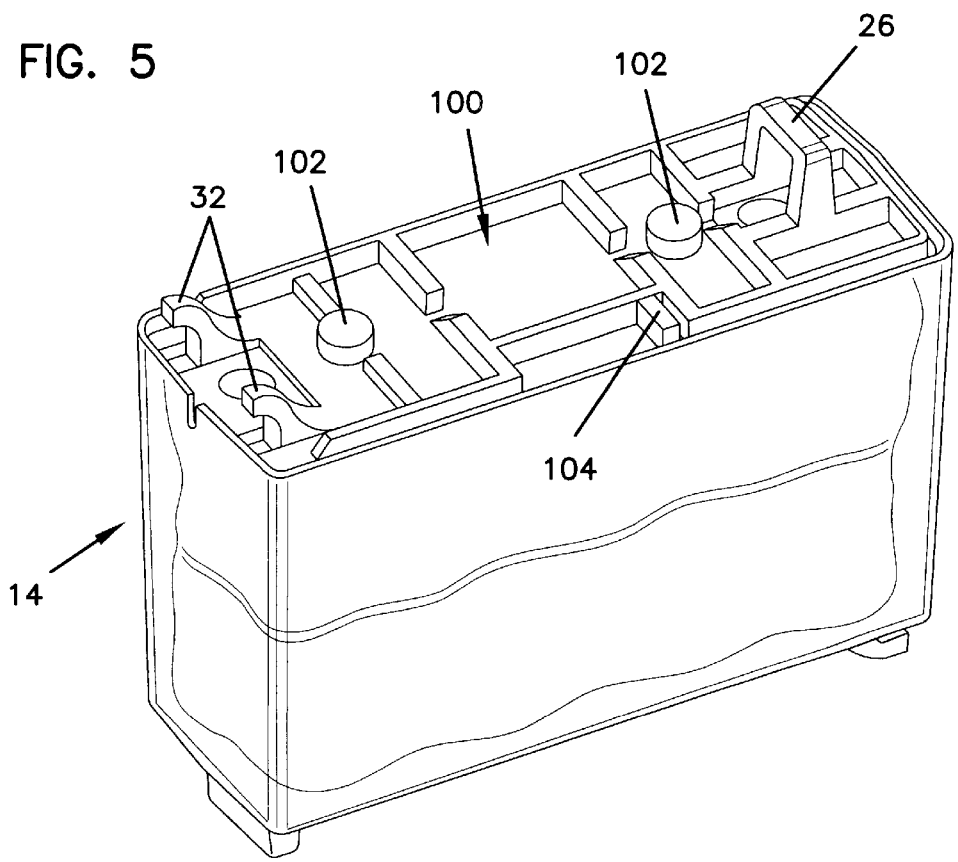
FIG. 5 is a perspective view of the bottom surface of the calibration cassette of FIG. 6 is a schematic diagram of a control system of the pump control module useful with the calibration cassette shown in FIGS. 4 and 5.

PATENT NO.     : 6,422,057 B1                                              Page 1 of 1
DATED          : July 23, 2002
INVENTOR(S)    : Anderson It is certified that error appears in the above-identified patent and that said Letters Patent is hereby corrected as shown below:

Column 3,
Line 27, "FIG. 5 is a perspective view of the bottom surface of the calibration cassette of          ." should read -- FIG. 5 is a perspective view of the bottom surface of the calibration cassette on FIG. 4, the bottom surface having a sensor testing mode cassette identification projection and two pressure protrusions; and --

Signed and Sealed this

Seventeenth Day of December, 2002

JAMES E. ROGAN
*Director of the United States Patent and Trademark Office*